US011699508B2

(12) United States Patent
Bendersky et al.

(10) Patent No.: US 11,699,508 B2
(45) Date of Patent: Jul. 11, 2023

(54) METHOD AND APPARATUS FOR SELECTING RADIOLOGY REPORTS FOR IMAGE LABELING BY MODALITY AND ANATOMICAL REGION OF INTEREST

(71) Applicant: MERATIVE US L.P., Ann Arbor, MI (US)

(72) Inventors: Marina Bendersky, Cupertino, CA (US); Tanveer Fathima Syeda-Mahmood, Cupertino, CA (US); Joy Tzung-yu Wu, San Jose, CA (US)

(73) Assignee: MERATIVE US L.P., Ann Arbor, MI (US)

( * ) Notice: Subject to any disclaimer, the term of this patent is extended or adjusted under 35 U.S.C. 154(b) by 768 days.

(21) Appl. No.: 16/700,137

(22) Filed: Dec. 2, 2019

(65) Prior Publication Data
US 2021/0166822 A1      Jun. 3, 2021

(51) Int. Cl.
*G16H 15/00*      (2018.01)
*G16H 50/70*      (2018.01)
(Continued)

(52) U.S. Cl.
CPC ......... *G16H 15/00* (2018.01); *G06F 18/2431* (2023.01); *G06N 5/04* (2013.01);
(Continued)

(58) Field of Classification Search
CPC ........ G16H 50/70; G16H 15/00; G16H 30/40; G16H 70/00; G06K 9/628; G06N 5/04; G06N 20/00
See application file for complete search history.

(56) References Cited

U.S. PATENT DOCUMENTS 7,475,062 B2    1/2009  de Souza
9,904,966 B2    2/2018  Mabotuwana et al.
(Continued)

OTHER PUBLICATIONS

Po-Hao Chen et al., "Integrating Natural Language Processing and Machine Learning Algorithms to Categorize Oncologic Response in Radiology Reports," J. Digit. Imaging 31:178-184 (Oct. 27, 2017) (Year: 2017).*

(Continued)

*Primary Examiner* — Jonathan Ng
*Assistant Examiner* — Benjamin L. Hanks
(74) *Attorney, Agent, or Firm* — Michael Best & Friedrich LLP

(57) ABSTRACT

Systems and methods for developing a classification model for classifying medical reports, such as radiology reports. One method includes selecting, from a corpus of reports, a training set and a testing set, assigning labels of a modality and an anatomical focus to the reports in both sets, and extracting a sparse representation matrix for each set based on features in the training set. The method also includes learning, with one or more electronic processors, a correlation between the features of the training set and the corresponding labels using a machine learning classifier, thereby building a classification model and testing the classification model on the reports in the testing set for accuracy using the sparse representation matrix of the testing set. The method further includes predicting, with the classification model, labels of an anatomical focus and a modality for remaining reports in the corpus not included in the sets.

16 Claims, 5 Drawing Sheets

(51) Int. Cl.
  *G06N 20/00* (2019.01)
  *G06N 5/04* (2023.01)
  *G16H 70/00* (2018.01)
  *G16H 30/40* (2018.01)
  *G06F 18/2431* (2023.01)
  *G06V 10/75* (2022.01)

(52) U.S. Cl.
  CPC .............. *G06N 20/00* (2019.01); *G06V 10/75* (2022.01); *G16H 30/40* (2018.01); *G16H 50/70* (2018.01); *G16H 70/00* (2018.01)

(56) References Cited

U.S. PATENT DOCUMENTS

| | | | |
|---|---|---|---|
| 10,176,645 | B2 | 1/2019 | Canfield et al. |
| 10,276,265 | B2 | 4/2019 | Reicher et al. |
| 2009/0228299 | A1* | 9/2009 | Kangarloo ............. G16H 30/40 707/999.005 |
| 2010/0099974 | A1 | 4/2010 | Desai |
| 2017/0337329 | A1 | 11/2017 | Liu et al. |
| 2018/0092696 | A1 | 4/2018 | Qian et al. |
| 2018/0107801 | A1 | 4/2018 | Guo et al. |
| 2018/0286504 | A1 | 10/2018 | Trovato |
| 2018/0365417 | A1 | 12/2018 | Wu et al. |
| 2019/0026106 | A1 | 1/2019 | Burton et al. |
| 2019/0074074 | A1 | 3/2019 | Trovato et al. |

OTHER PUBLICATIONS

Sohrab Towfighi et al., "Labelling chest x-ray reports using an open-source NLP and ML tool for text data binary classification," medRxiv.org, posted Nov. 22, 2019 (https://www.medrxiv.org/content/10.1101/19012518v1) (Year: 2019).*

John Zech et al. "Natural Language—based Machine Learning Models for the Annotation of Clinical Radiology Reports," Radiology 287:2 570-580, May 2018 (Year: 2018).*

Tianrun Cai et al., "Natural Language Processing Technologies in Radiology Research and Clinical Applications," Radiographs 2016, 36:176-191, 2016 (Year: 2016).*

Zech, John et al., "Natural Language-based Machine Learning Models for the Annotation of Clinical Radiology Reports", Radiology, vol. 287, No. 2, May 2018, pp. 570-580.

Pham, Anne-Dominique et al., "Natural language processing of radiology reports for the detection of thromboembolic diseases and clinically relevant incidental findings", BMC Bioinformatics, vol. 15, No. 266, 2014, (10 pages).

Yetisgen-Yildez, Meliha et al., "A text processing pipeline to extract recommendations from radiology reports", Journal of Biomedical Informatics, vol. 46, pp. 354-362, 2013.

Nguyen, Dung D H et al., "Supervised machine learning and active learning in classification of radiology reports", J Am Med Inform Assoc, vol. 21, pp. 893-901, 2014.

* cited by examiner

The lungs show no evidence of infiltrates or effusions. The heart size is grossly within normal limits.
No evidence of definite acute bony abnormalities are noted. No evidence of acute intrathoracic pathology.
Signed Electronically By: Dr. [PERSONALNAME] – [ALPHANUMERICID] – [DATE]:55 AM

FIG. 1A

ADMITTING [PERSONALNAME]: [PERSONALNAME] LAC
PROCEDURE: BCT [ADDRESS] WO [PERSONALNAME]
Acc #: [ALPHANUMERICID] Date: Mar [DATE] CPT: [ALPHANUMERICID]
PROCEDURE: CHEST [ADDRESS] WO [PERSONALNAME]
CLINICAL INDICATION:
Left-sided chest pain. [PERSONALNAME].
COMPARISON:
None.
TECHNIQUE:
Chest [ADDRESS] without contrast
DISCUSSION:
Mediastinum:
The heart is normal in size and calcified coronary atherosclerosis.
Aneurysmal dilation of the descending thoracic aorta which measures up to 4.9 cm in diameter.
Calcified aortic atherosclerosis.
No mediastinal or axillary adenopathy.
Lungs/pleura:
Mild airspace opacity in the right lung base may be due to atelectasis.
Upper abdomen:
Cholelithiasis.
Bones/soft tissues:
No acute osseous abnormalities.
IMPRESSION:
1. Aneurysmal dilation of descending thoracic aorta which measures up to 4.9 cm in diameter.

FIG. 1B

Indication: Cough.
Correlation is made to report of chest x-ray dated [DATE].
No prior study is available for comparison.
There is no evidence of airspace consolidation. There is a 4 mm calcified pulmonary granuloma in the periphery of the right upper lobe. There is no pleural effusion of pneumothorax. There is mild to moderate cardiomegaly with postoperative changes from previous mediastinotomy and CABG.
The pulmonary vasculature is within normal limits. There is calcification of the aortic arch and descending thoracic aorta. There are mild to moderate degenerative changes of the thoracic spine.

CONCLUSION:
NO ACUTE PULMONARY PROCESS
CARDIOMEGALY WITH POSTOPERATIVE CHANGES FROM PRIOR CABG. THE FINDINGS WERE DISCUSSED WITH [PERSONALNAME], MD ON [DATE] AT [DATE]:41 P.M.

FIG. 1C

METHOD AND APPARATUS FOR SELECTING RADIOLOGY REPORTS FOR IMAGE LABELING BY MODALITY AND ANATOMICAL REGION OF INTEREST

FIELD

Embodiments described herein relate to systems and methods for mining data using machine learning-based model predictions that are accurate and useful. For example, some embodiments relate to creating and using a machine learning classifier, such as a logistic regression classifier, to predict labels of anatomical regions of interest and modality for radiology reports.

SUMMARY

Large data collections, which can be comprised of text, images or even video, are becoming more easily available to researchers, clinicians and the public in general. It is quite often necessary, as a critical initial step, to mine input data before proceeding to further research or analysis, such as using the data as training data for building models via machine learning techniques.

For example, in a research setting, careful and accurate data labeling can be a tedious and time-consuming task that often requires manual inputs and expert knowledge. Moreover, the same dataset might need to be relabeled multiple times, not only in cases where the same dataset is used for different research purposes but also in cases where the data is mislabeled. Mislabeled data produces in itself at least two new problems; first, the mislabeled data needs to be identified and differentiated from correctly labeled data, and second, the mislabeled data should be corrected or removed from the dataset (if possible). Models trained with mislabeled data will most certainly yield low performance metrics.

Accordingly, image labeling is an important problem to solve for using machine learning on large sets of data, including medical image data. In particular, since medical images are specialized images, these images cannot be simply crowdsourced as for other types of images, such as scene images. Also, it is important to select relevant images for machine learning projects. In particular, since picture archiving and communication systems (PACS) contain images associated with many types of imaging modalities and many different anatomical regions, the images must be classified to recognize these regions reliably to begin the labeling process for images (e.g., to build training and optionally testing data for the machine learning process). However, manually sorting through images and/or associated radiology reports to select relevant images and/or reports for labeling is a time intensive undertaking, especially for large set of images or associated reports, which may include tens or hundreds of thousands of images and/or associated reports.

Researchers have conducted natural language processing (NLP) and machine learning studies on reports of different imaging modalities or pertaining to different medical specialties. Each of these studies, however, is concerned with the analysis of reports of only one imaging modality and only one body anatomy. Given the availability of large collections of reports, comprising multiple imaging studies on multiple anatomies, embodiments described herein approach the broader problem of classifying the type of reports, by, in some embodiments, identifying jointly the imaging modality of the procedure and the body anatomy being imaged. For example, as described in more detail below, embodiments described herein address the problem of classifying radiology reports for which the type of procedure and/or the body anatomy imaged cannot be determined systematically, and, instead, requires manual and detailed evaluation. This issue can occur when incoming data from hospitals (received through gateways) needs to be sorted and categorized. Often, the only way to know the content of a radiology report is by actually opening the specific file. Accordingly, manually opening and reviewing such reports is problematic for large amounts of data. Thus, embodiments described herein simultaneously determine modality and anatomical region for reports through automated means.

For example, the imaging modality of the exams described in the reports shown in FIGS. 1A, 1B, and 1C can only be inferred by manual examination of the report text itself. The descriptions of lungs, heart, and bones in FIG. 1a suggest the imaging modality is a chest X-ray (CXR), though this is not explicitly included in the text and, therefore, the label could not have been inferred with a simple keyword matching approach. The structured text report shown in FIG. 1b suggests the exam is a chest computed tomography (CT), due to the presence of the words "CT," "Chest," and "contrast." However, in this case, it is not straightforward to obtain the "chest CT" label with a keyword matching approach since the relevant tokens are not contiguous and are mentioned in different sections of the report. In particular, the relevant text "chest without contrast" in the technique section is ambiguous, since it could imply a chest CT without contrast or a chest MRI without contrast. The example report shown in FIG. 1c is also ambiguous. On one side, the report could correspond to a CXR report (a chest X-ray is mentioned as a reference study). However, on the other hand, the content of the report itself describes a "4 mm calcified pulmonary granuloma," which is more often and more clearly visualized in a chest computed tomography (CT), which is a form of a priori knowledge.

Accordingly, embodiments described herein classify radiology reports by inferring, jointly, the imaging modality of the procedure and the body anatomy being imaged. This information can be used in various ways. For example, in the absence of a structured report database or when reports become available without the corresponding images, the automatic extraction of imaging modality and anatomy imaged can be used as an initial step that enables, for instance, a quick determination of follow-up procedures or treatment. The extracted information is also useful in the development of applications that improve the clinical workflow, such as summarization or medical information retrieval tools.

For example, one embodiment provides a method for developing a classification model. The method includes, selecting, from a corpus of reports, a subset of the reports from which to form a training set and a testing set, assigning labels of a modality and an anatomical focus to the reports in both the training set and the testing set, and extracting a sparse representation matrix for each of the training set and the testing set based on features in the training set. The method also includes learning, with one or more electronic processors, a correlation between the features of the training set and the corresponding labels using a machine learning classifier, thereby building a classification model, and testing the classification model on the reports in the testing set for accuracy using the sparse representation matrix of the testing set. In addition, the method includes predicting, with the classification model, labels of an anatomical focus and a modality for remaining reports in the corpus not included in the subset.

Another embodiment provides a system for developing a classification model. The system includes one or more electronic processors. The one or more electronic processors are configured to select, from a corpus of reports, a subset of the reports from which to form a training set and a testing set, assign labels of a modality and an anatomical focus to the reports in both the training set and the testing set, and extract a sparse representation matrix for each of the training set and the testing set based on features in the training set. The one or more electronic processors are also configured to learn a correlation between the features of the training set and the corresponding labels using a machine learning classifier, thereby building a classification model and test the classification model on the reports in the testing set for accuracy using the sparse representation matrix of the testing set. In addition, the one or more electronic processors are configured to predict, with the classification model, labels of an anatomical focus and a modality for remaining reports in the corpus not included in the subset.

Yet another embodiment provides a non-transitory, computer-readable medium storing instructions that, when executed by one or more electronic processors, perform a set of function. The set of functions includes selecting, from a corpus of reports, a subset of the reports from which to form a training set and a testing set, assigning labels of a modality and an anatomical focus to the reports in both the training set and the testing set, and extracting a sparse representation matrix for each of the training set and the testing set based on features in the training set. The set of functions also includes learning a correlation between the features of the training set and the corresponding labels using a machine learning classifier, thereby building a classification model, testing the classification model on the reports in the testing set for accuracy using the sparse representation matrix of the testing set, and predicting, with the classification model, labels of an anatomical focus and a modality for remaining reports in the corpus not included in the subset.

Other aspects of the embodiments will become apparent by consideration of the detailed description and accompanying drawings.

BRIEF DESCRIPTION OF THE DRAWINGS

FIGS. 1A, 1B, and 1C illustrate examples of radiology reports in which the type of report cannot be identified systematically.

DETAILED DESCRIPTION

Figure 2:
FIG. 2 illustrates a distribution of radiology report classifications.

Before any embodiments are explained in detail, it is to be understood that the embodiments are not limited in their application to the details of construction and the arrangement of components set forth in the following description or illustrated in the following drawings. Other embodiments are capable of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the embodiments. In addition, embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the embodiments may be implemented in software (e.g., stored on non-transitory computer-readable medium) executable by one or more processors. As such, it should be noted that a plurality of hardware and software based devices, as well as a plurality of different structural components, may be utilized to implement the embodiments. For example, "mobile device," "computing device," and "server" as described in the specification may include one or more electronic processors, one or more memory modules including non-transitory computer-readable medium, one or more input/output interfaces, and various connections (e.g., a system bus) connecting the components.

As described above, embodiments described herein provide systems and methods for developing a classification model for classifying radiology reports, which can be used to predict anatomical focus and modality labels for radiology reports. Once labeled or classified, these reports (and the associated images) can be used in various ways, such as for training or testing data for deep learning applications. As described herein, a number of different classification models are discussed, based on machine learning and on natural language processing (NLP), that achieve high performance in both binary and multiclass classification tasks. As also discussed below, the models yield an average F1 score of around 0.9. Thus, the models readily help save resources that would otherwise be spent on the expensive task of data labeling and classification. These models can also provide classification baselines to be used for comparison in the development of more complex approaches.

I. Methods

Some of the methods described herein implement machine learning models to tackle the general problem of data classification (data labeling), which is often the immediate and essential task that researchers need to complete when large amounts of data are available. Depending on the specific research problem, researchers might be interested in identifying one particular class or many classes. For the cases in which the goal is to distinguish only one class from the rest, it is appropriate to train binary classifiers that will distinguish between such a class of interest and the rest of the classes as a whole. For cases in which there are multiple classes of interest, the analogous methodology consists in training multiclass classification models.

The data used for the comparative study described herein comprises radiology text reports (no imaging data). Also, the data classification problem was approached by defining two tasks: the binary classification task and the multiclass classification task. For the binary classification task, chest X-ray reports (CXR reports) are distinguished from non-chest X-ray reports (non-CXR reports). The methodologies (and results) are presented for the CXR/non-CXR classification in particular, but they can be generalized to other binary classification tasks. For the multiclass classification task, 21 classes of reports were defined (such as, for example, mammography, chest X-ray, obstetric ultrasound, spine magnetic resonance imaging (MM), spine X-ray, bone densitometry analysis (DEXA), chest, abdomen and pelvis computed tomography (cap CT), abdomen ultrasound, leg venous Doppler ultrasound, feet and ankle X-ray, positron-emission tomography PET/CT tumor imaging, chest computed tomography (chest CT), breast ultrasound, knee MRI, hip X-ray, knee X-ray, brain MRI, breast MM, and thyroid ultrasound), and machine learning algorithms were implemented to efficiently distinguish between them.

The binary classification task was approached by implementing logistic regression, decision tree classifiers, and support vector machine (SVM) classifiers. The performance of these classifiers is evaluated below on sets of training data and of testing data. A NLP-based heuristic model is also discussed here and the performance of this model is compared to that achieved by machine learning-based classifiers (ML-based classifiers).

Similarly, the multiclass classification task was approached by implementing logistic regression, decision tree classifiers, and SVM classifiers. These implementations followed the "one-vs-rest" paradigm, which involves the fitting of $k=n_{classes}$ binary classifiers.

A. Machine Learning Models

For the evaluations described herein, the machine learning (ML) classifiers were implemented using the scikit-learn package in Python and were trained on a dataset of 750 labeled reports and tested on a dataset of 250 labeled reports.

For binary classification, two logistic regression classifiers were considered, each of which was trained with either term-frequency (word-count) features or term frequency-inverse document frequency (TFIDF) features. These models were regularized (C=1) and each of the classes were assigned equal weights. The decision tree classifiers for binary classification were similarly trained with word-count features and each of the nodes in the tree was expanded until the leaves are "pure," indicating that navigating a specific branch will lead to only one possible class (i.e., no restriction on the maximum depth of the tree is imposed).

Also, for the binary classification task, the predictions of the SVM classifier are based on a linear kernel given by $$k(x,y)=x^T y+c,$$

where x is the training example, y is the test example and c is a constant. The first term in the above equation represents the inner product $<x, y>$. The features used in the SVM classifiers described herein are word counts.

A SVM classifier is a learning model that constructs a hyperplane in the feature space such that the separation distance (or margin) between such hyperplane and the nearest data point of any class is maximized. SVM classifiers are a type of kernel method, such that rather than learning fixed weight features, a SVM model learns a specific weight $w_i$ for the specific training example $x_i$. The prediction of an unlabeled test example is based on a similarity function k, or kernel, applied to the unlabeled example $y_i$ and the training example $x_i$.

With respect to the multiclass classification task, the models were trained with 701 labeled reports, and the features were word counts. As noted above, all these models follow the paradigm "one-vs-rest" (ovr), which consists of training k binary classifiers where $k=n_{classes}$. In particular, for each example report, the models yield its probability of belonging to each of the 21 classes and the predicted class is that with the highest probability.

Ovr strategies can be contrasted with "one-vs-one" (ovo) strategies. In the latter, binary classifiers are trained for each pair of classes, resulting in a more computationally expensive model since this involves the training of $(k(k-1))/2$ classifiers. Given an example report, each binary classifier outputs a vote for either of two possible classes and the final prediction is derived from the majority of such votes.

In the multiclass classification task, the ovo approach was tested and a meaningful difference in performance with respect to ovr-based implementations was not found. In terms of computational costs, however, the running time of the ovo approach is $O(k^2)$, while for the ovr approach it is only $O(k)$. The difference in running times increases rapidly with increasing number of classes (k). Therefore, the multiclass classification evaluations described herein were performed following an ovr approach, but it should be understood that other approaches may be used in some situations.

B. NLP-Based Empirical Model

To obtain a baseline with which to compare ML-based predictions, a NLP-based model was developed that relies on the observed distribution of terms that are most frequently used in CXR reports. In particular, a difference was observed between the frequency of these terms in CXR reports and the respective frequency in non-CXR reports. In this section, this difference is quantified to derive a numerical threshold that can be used in the binary classification task.

For the NLP model, the training dataset of 750 labeled reports contained 81 CXR reports. The complete text in each of these reports was pre-processed as described herein and all the processed reports were joined to compose a "CXR corpus." Within this CXR-corpus, all bigrams that appear at least five times and are composed of words that have at least three characters, none of which is numeric, were identified. Trigrams were also identified in the corpus, though a lower limit was no imposed on the frequency of trigrams since trigrams are repeated less frequently than bigrams. However, each of the three words in each trigram had at least two characters, none of which were numeric.

By detailed observation of the reports in the CXR-corpus, an arbitrary list was compiled of 63 "CXR-terms" that were most frequently encountered in such reports. Some terms included in this list were "chest," "two," "views," "lung," "clear," "pleural," "effusion," etc. The bigram and trigram lists were then filtered by selecting only bigrams and trigrams that contained at least one of the terms included in the list. This filtering obtained bigrams and trigrams that are expected to be representative of text present in CXR-reports. This analysis, as performed on the training dataset resulted in 99 "CXR-bigrams" and 1,327 "CXR-trigrams."

To train the NLP-based algorithm, a percentage of CXR-bigrams and CXR-trigrams was calculated for each of the reports in the training dataset. These percentages represented the proportion of CXR-bi(tri)grams out of all bi(tri)

grams present in the report, whether it was labeled as a CXR report or as a non-CXR report. Table I, below, illustrates the percentages of CXR N-grams found in the training data for each type of report and each type of CXR N-gram.

TABLE I

| Report type | CXR-bigrams (%) | CXR-trigrams (%) |
| --- | --- | --- |
| Chest X-ray | 0.222 ± 0.0953 | 0.423 ± 0.103 |
| other | 0.0141 ± 0.0185 | 0.0142 ± 0.0203 |

The distribution of CXR N-grams for each report type and each N-gram type are presented in Table 1 as intervals (mean±std. dev).

As seen in Table I, in non-CXR reports, the average proportion of CXR N-grams remained fairly constant and those proportions vary strongly between reports, given the high standard deviation. In CXR reports, the standard deviations are not only lower than the averages for both types of CXR N-grams, but the average percent of CXR trigrams (0.423) is almost double than the average percent of CXR bigrams (0.222).

In addition, a two sample t-test was performed to reject (or fail to reject) the null hypothesis that the mean percentage of trigrams in CXR-reports equals the respective value for non-CXR reports (i.e., $\mu_{CXR, \, tri\text{-}grams} = \mu_{non\text{-}CXR, \, tri\text{-}grams}$). The sample sizes of CXR and non-CXR reports were $n_{CXR}=81$ and $n_{non\text{-}CXR}=669$, and the average percentages and sample standard deviations of trigrams are presented in the third column in Table I. The two-tailed test at the 5% significance level yields $p_{value}$ less than 0.05. Therefore, the null hypothesis that the mean percents of trigrams are equal in CXR and non-CXR reports can be rejected.

To derive a numerical threshold that can be used in the classification of unseen reports, the gap (for each type of N-gram) between the upper limit in non-CXR reports and the lower limit in CXR reports can be calculated. Since this gap is wider in the case of trigrams, a mid-point of such a gap was calculated, which had a value of about 0.17. Based on this numerical limit, an empirical threshold for the binary classification task of 0.2 was established. Namely, for each unseen radiology report, the percent of CXR-trigrams (out of all trigrams present in the report) was calculated. If the percent of CXR-trigrams was greater than 20%, the unseen report was classified as a CXR report; otherwise, it was labeled as a non-CXR report.

The presented NLP-based model was applied to the CXR/non-CXR binary classification and was not extended to the multiclass classification problem. However, such an extension is technically straightforward given the availability of a dataset with multiple types of radiology reports (preferably the same 21 classes defined herein) and definitions of class-specific vocabularies and empirical thresholds. Those definitions could become a prohibitive task when $n_{classes}=21$ and even more so as the number of classes increases.

C. Data Pre-Processing and Construction of Feature Vectors

The radiology reports analyzed by the models described herein are text files, and may sometimes contain different sub-sections, such as, for example, "History," "Findings," or "Impression." To avoid overfitting the models to the specific style adopted by particular radiologists or medical institutions, the complete text report was analyzed.

From a collection that includes approximately 140,000 radiology reports, 1,000 of those reports were randomly selected and a label was assigned (manually) to each of those 1,000 reports. The reports in this collection were collected from eight different imaging centers. To account for differences in report writing structures and styles and in the frequency of specific exams (such as CXR, chest CT, Mammography, spine MM) performed at each imaging center, the distribution of reports from each imaging institution in the original dataset was preserved in the labeled sample of 1,000 reports.

FIG. 2 shows a distribution of the 21 report classes distinguished in the multiclass classification problem. Percentages of reports of each class are presented for the complete dataset (1000 reports), the training data (701 reports) and the testing data (299 reports). The abbreviation "US" stands for "ultrasound," "DEXA" refers to Bone Densitometry Analysis, and "cap CT" indicates "chest, abdomen and pelvis CT" (distinguished from "ChestCT"). Other report classes are mammography, chest X-ray (CXR), obstetric ultrasound, spine magnetic resonance imaging (MM), spine X-ray, bone densitometry analysis (DEXA), chest, abdomen and pelvis computed tomography (cap CT), abdomen ultrasound, leg venous Doppler ultrasound, feet and ankle X-ray, positron-emission tomography PET/CT tumor imaging, chest computed tomography (chest CT), breast ultrasound, knee MM, hip X-ray, knee X-ray, brain MRI, breast MRI, and thyroid ultrasound.

For the binary classification task, labels of "CXR" or "non-CXR" were assigned to each report in the sample of 1,000 reports. The non-CXR reports described studies performed using a different imaging technique and/or a different anatomy. The binary-labeled reports were then randomly split into training and testing datasets, which contained, respectively, 750 and 250 reports. The proportions of CXR reports in the training and testing datasets were also verified to be approximately 10%, which is in agreement with the respective proportion in the complete labeled sample of 1,000 reports.

The pre-processing of the report text included the removal of punctuation, non-alphanumeric characters, de-identification tags, and common headers and footers. The pre-processing also included the extraction of a sparse representation matrix for the testing set and the training set. This extraction was performed based on features in the training set, such as, for example, term-frequency (word count) features or term frequency-inverse document frequency (TFIDF) features. To obtain term frequency features, the processed text was converted to a sparse matrix of token counts and the resulting sparse matrix, for the particular data sets, contained 7,826 word-count features. Using TFIDF features, each of the word counts was replaced by the scaled frequency of the term, which also resulted, for the particular data sets, a sparse matrix of 7,826 features.

For the multiclass classification task, 21 classes of radiology reports were defined. These classes were selected by re-labeling each of the non-CXR reports with a more informative label, such as, for example, "SpineXray," "Mammography," or "chestCT." The 20 most frequent labels were also selected and the remaining reports, not belonging to any of these 20 classes were assigned to the category "other."

After the pre-processing was complete, the complete set of 1,000 reports was split using a 70/30 random split, to obtain a training dataset of 701 files and a testing dataset of 299 files. This random split was verified to ensure an approximately equal representation of each class in each dataset. The respective class distributions are as shown in FIG. 2.

TABLE II

| Classifier | Precision | Recall |
|---|---|---|
| Logistic regression (word count features) | 0.96 ± 0.14 | 0.95 ± 0.12 |
| Logistic regression (TFIDF features) | 1.00 ± 0.00 | 0.46 ± 0.44 |
| Decision tree | 0.90 ± 0.23 | 0.85 ± 0.24 |
| SVM (linear kernel) | 0.94 ± 0.16 | 0.97 ± 0.10 |
| NLP-based | 0.98 | 1.00 |

TABLE II, above, shows precision and recall obtained in the binary classification of 750 training examples. For each algorithm, the results are averages of the performance in 10-fold cross validation and presented as 95% confidence intervals (avg±1.96*std. dev). The NLP-based classifier was evaluated on the complete collection of 750 training examples (no CI is reported in this case).

TABLE III

| Classifier | Precision | Recall | F1 | AUC |
|---|---|---|---|---|
| Logistic regression (word count features) | 1.00 | 1.00 | 1.00 | 1.00 |
| Logistic regression (TFIDF features) | 1.00 | 0.67 | 0.8 | 0.83 |
| Decision tree | 1.00 | 0.96 | 0.98 | 0.98 |
| SVM (linear kernel) | 0.96 | 1.00 | 0.98 | 0.998 |
| NLP-based | 0.81 | 0.96 | 0.88 | N/A |

TABLE III, above, shows precision, recall, F1 and area under curve (AUC) scores for the binary classification of 250 test examples. The decision threshold in the NLP-based classifier is fixed at 0.20 so an area under the curve (AUC) score is not defined in this case (reported as N/A).

II. Evaluation Results

After training all machine learning and NLP-based models, the performance of each classifier was evaluated in each of the binary and multiclass classification tasks of various datasets. Performance was evaluated by metrics such as precision, recall, F1 score, and AUC score.

A. Evaluation on the Development Dataset

1) Binary Classification

The performance of each of the binary classifiers was first evaluated in the training dataset (750 reports) with a 10-fold cross validation strategy. By iterating over the data 10 times, a cross-validation strategy allows for the calculation of confidence intervals for the precision and the recall, and, thus, provides more accurate estimates of the classifiers' performance on the test data. For each ML-based classifier described above, the 95% confidence intervals of the precision and the recall are presented in Table II. To evaluate the NLP-based approach, however, cross-validation was not performed because this method is based on a single numerical threshold. In this case, confidence intervals are not relevant since the precision and the recall were calculated once on the entire training dataset.

Similar to the results presented in Table II, Table III reports the performance metrics of those same classifiers on the test dataset of 250 reports. The metrics reported in Table III are precision, recall, F1, and AUC scores. A comparison of Tables II and III shows that the cross validation values represent accurate estimates of the classifiers' performance in the testing dataset.

As reported in Table III, all classifiers yield high precision, with the lowest value of 0.81 obtained by implementing the NLP-based model. Recall values are also high (above 0.96), except for the low value of 0.67 obtained with the logistic regression classifier trained with TFIDF features. Also, better classification performance was obtained with the use of word count features than with TFIDF features (compare the first two rows in Table III). While TFIDF features are useful in many contexts to decrease the weight of frequent words, such as articles and prepositions, it is possible that the frequent words in a specific class of radiology reports are actually the differentiating factors between classes. Therefore, reducing the weight of these frequent domain-specific words might increase the similarity between reports that are actually of different types. This effect could be related to the decrease in recall observed with the use of TFIDF features. In addition, the logistic regression classifier trained with word count features yields perfect performance metrics (all metrics are equal to 1).

2) Multiclass Classification

The performance of multiclass classification algorithms on the test dataset of 299 reports is shown in Table IV, below. Metrics such as precision, recall and F1 scores were computed by either "micro" or "macro" averaging. A micro-average implies that the metrics were calculated globally for all instances, treating them equally and not taking into account their particular class. A macro-average, inversely, involves the calculation of metrics for each class separately followed by the unweighted mean of those metrics. The features in all of these multiclass classifiers are word counts and the SVM kernel is linear.

The micro- and macro-performance metrics in Table IV show that the logistic regression and SVM models outperform the decision tree classifier. The linear classifiers (logistic regression, SVM) achieve a F1 score of approximately 0.90, while the analogous value for the decision tree classifier is of approximately 0.82. It is noted that such scores hardly vary with the specific type of averaging. A strict comparison of the micro- and macro-F1 scores achieved with logistic regression and SVM classifiers, indicates that the logistic regression classifier slightly outperforms the SVM classifier.

Figure 3:
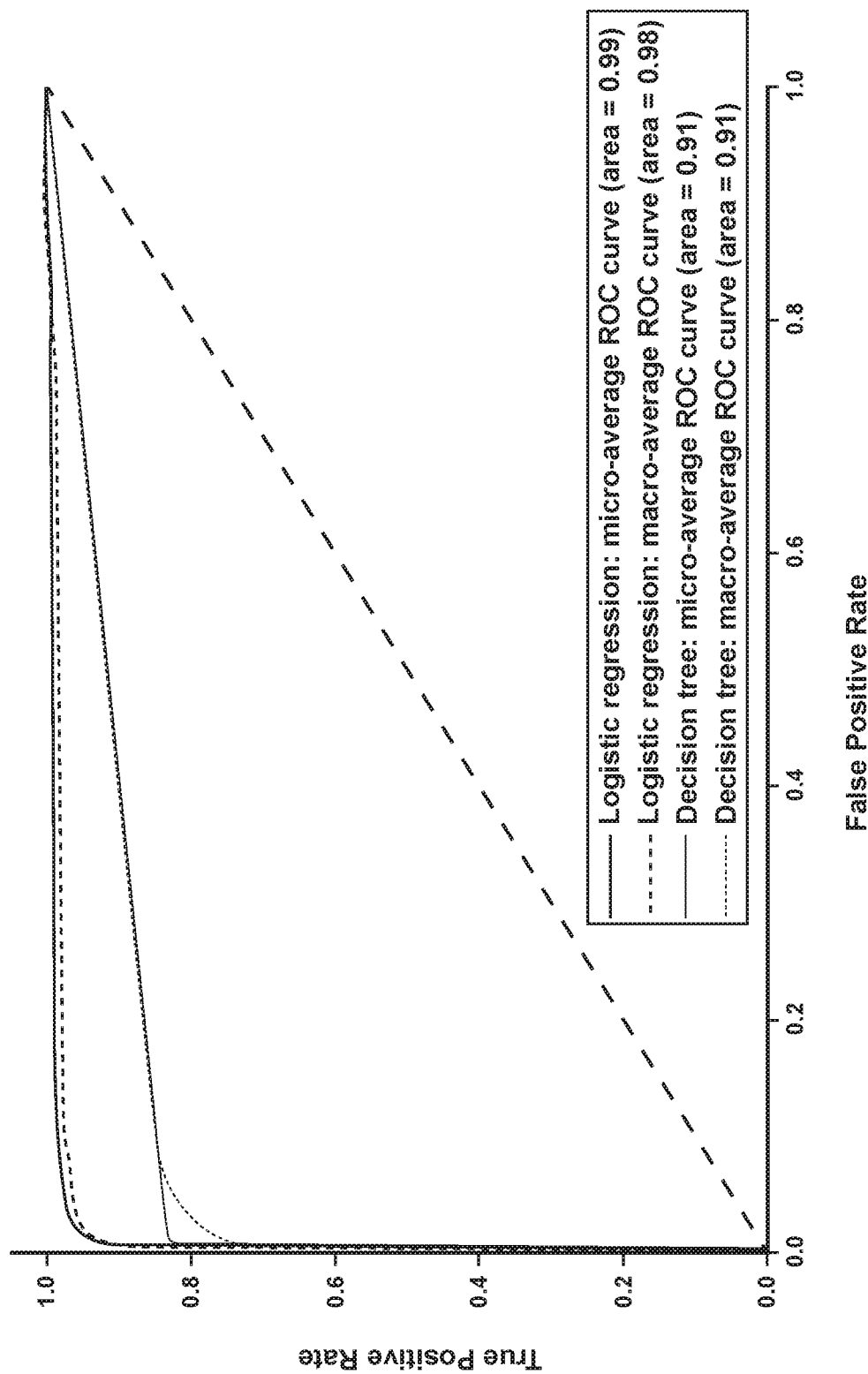
FIG. 3 illustrates micro and macro average receiver operating characteristic (ROC) curves for logistic regression and decision tree classifiers.

FIG. 3 shows micro-average and macro-average receiver operating characteristic (ROC) curves for the multiclass classification of reports with the logistic regression and decision tree classifiers. In particular, FIG. 3 compares the micro-average and macro-average ROC curves obtained with the "best" performing classifier (i.e., logistic regression) and the "worst" performing classifier (i.e., decision tree). As expected from the metrics reported in Table IV, the AUC values for the logistic regression classifier are larger than those for the decision tree classifier, i.e., AUC (log. reg)$_{micro, macro}$=0.99, 0.98 while AUC (dec. tree)$_{micro, macro}$= 0.91, 0.91.

TABLE IV

| Classifier | Precision (micro-avg) | Recall (micro-avg) | F1 score (micro-avg) | Precision (macro-avg) | Recall (macro-avg) | F1 score (macro-avg) |
|---|---|---|---|---|---|---|
| Logistic regression (word count features) | 0.9097 | 0.9097 | 0.9097 | 0.9202 | 0.893 | 0.896 |
| SVM (word count features, linear kernel) | 0.906 | 0.906 | 0.906 | 0.899 | 0.896 | 0.887 |

TABLE IV-continued

| Classifier | Precision (micro-avg) | Recall (micro-avg) | F1 score (micro-avg) | Precision (macro-avg) | Recall (macro-avg) | F1 score (macro-avg) |
|---|---|---|---|---|---|---|
| Decision tree (word count features) | 0.829 | 0.829 | 0.829 | 0.844 | 0.833 | 0.827 |

TABLE IV, above, shows precision, recall, and F1 scores for the multiclass classification (21 classes) of 299 test reports. For each classification algorithm, micro-metrics, computed by considering all instances equally, and macro-metrics, obtained by considering all classes equally are reported.

TABLE V

| Classifier | Precision | Recall | F1 score |
|---|---|---|---|
| Logistic regression (word count features) | 0.929 | 0.914 | 0.9214 |
| SVM (word count features, linear kernel) | 0.935 | 0.812 | 0.869 |
| NLP-based | 0.985 | 0.0249 | 0.0486 |

TABLE V above provides a comparison of the performance of logistic regression, linear SVM and NLP-based models applied to the binary classification of 522,279 labeled radiology reports that are part of the MIMIC database, which is a freely accessible critical care database. In each case precision, recall, and F1-score values are reported.

B. Evaluation on Data from Other Sources

To estimate the robustness of the binary classifiers more accurately, a publicly available dataset was selected that was not seen in any of the training (or testing) phases of any of the classifiers. This dataset was part of the MIMIC database. Starting with the NOTE EVENTS table in this database, only RADIOLOGY reports were selected, which provided a database of 522,279 reports. These reports also include a DESCRIPTION attribute, which is essentially the type of report, or, for purposes of this evaluation, their classification label. Performance metrics for the binary classification of the MIMIC dataset are reported in Table V above. Table V presents precision, recall, and F1 score values achieved with logistic regression, SVM, and NLP-based classifiers. As noted in Table V, the features of the ML-based models are word counts, and the SVM kernel is linear.

As shown in Table V, the highest precision of approximately 0.94 is achieved with the SVM classifier, while the logistic regression classifier yields the highest recall of approximately 0.91. Overall, the best performance is achieved with the logistic regression classifier, which yields an F1 score of 0.92.

The NLP-based model yields performance metrics that clearly exemplify the precision-recall trade-off. In other words, the precision obtained in this case is extremely high and the recall is extremely low, to yield a remarkably low F1 score of approximately 0.05. As described above, this model is based on manually designed CXR-trigrams that were particularly fit to a specific dataset. Accordingly, if these CXR-trigrams represent at least 20% of the overall trigrams in the test report, the latter is a CXR report. Inversely, the NLP-model does not consider all other (possibly infinite) CXR-trigrams that could be defined for other report collections, or, it is also possible that the threshold should be lower for such collections to reduce the number of false negatives. These observations could help explain the results of very high precision and very low recall obtained in the classification of the MIMIC dataset.

As noted above, the results in Table V indicate that the best classification performance is obtained with the logistic regression classifier. Therefore, this classifier was selected for the analysis of data collected from other sources, different from those of the data used to train the classifiers. These datasets will be referred to herein as datasets 'A,' 'B,' and 'C.'

Figure 4:
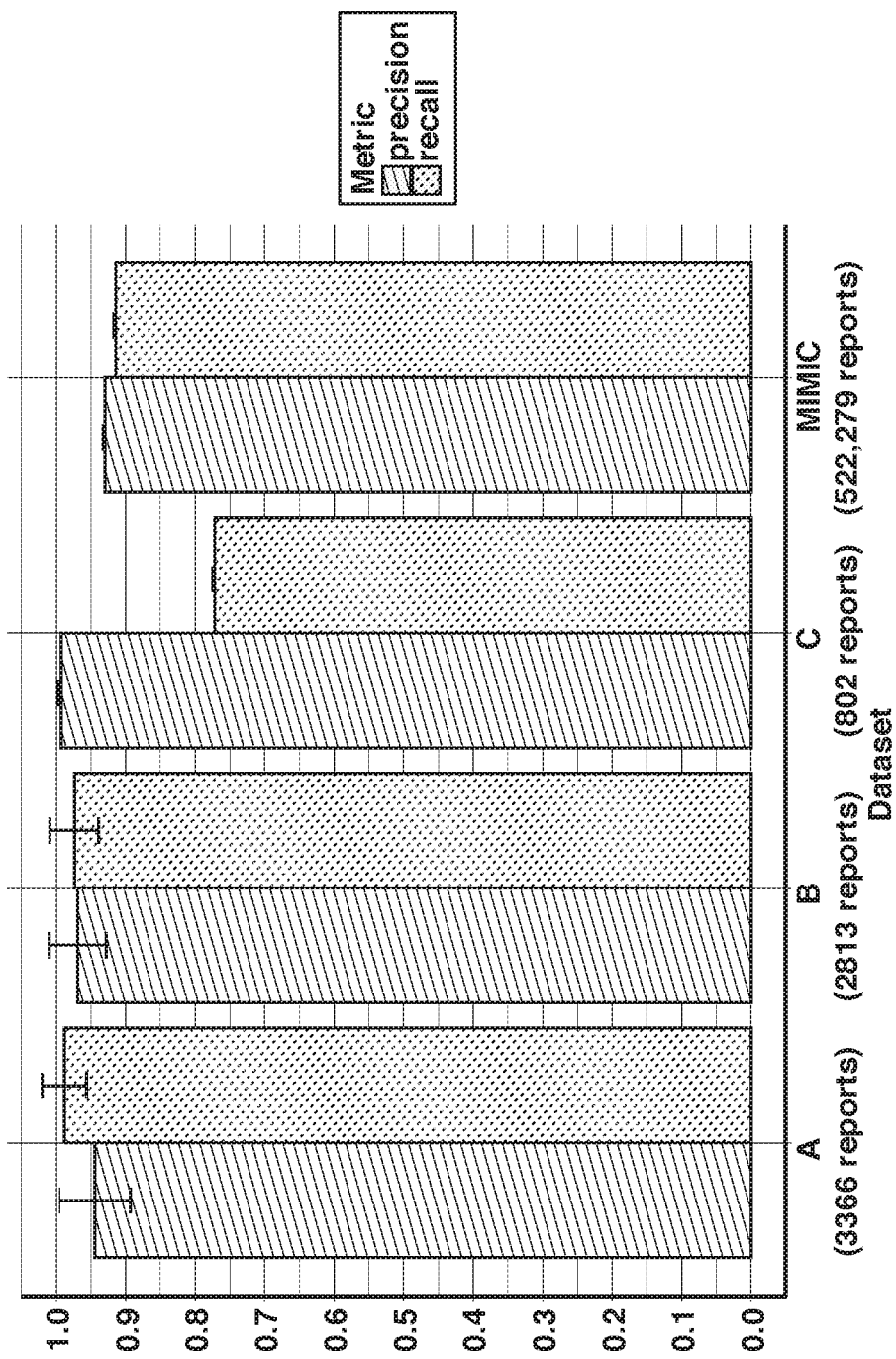
FIG. 4 illustrates a graph showing performance of the logistic regression classifier on data sets from different sources.

FIG. 4 illustrates the performance of the logistic regression classifier (with word count features) on datasets from different sources. Precision and recall are presented as 95% confidence intervals for datasets 'A' and 'B' because the metrics were calculated on random samples from the complete dataset. Datasets 'C' and MIMIC are labeled so the metrics in those cases are computed for all of the reports.

In particular, FIG. 4 shows the performance metrics of the logistic regression classifier (with word count features) obtained in the classification of reports in the datasets 'A,' 'B,' and 'C.' For a visual comparison, the performance of the classification of the MIMIC dataset is also presented, which is also reported in the first row in Table V.

Given the size of the unlabeled collections 'A' and 'B,' which comprised 3,366 and 2,813 reports, respectively, the classifier's performance was evaluated by selecting 10 random samples of 100 reports each and labeling each of those reports manually. The precision and recall were calculated for each sample and the respective 95% confidence intervals are shown in the bars labeled 'A' and 'B' in FIG. 4. Dataset 'C' and the MIMIC dataset are labeled datasets, so random sampling is not required and the metrics were computed on the complete datasets.

With the exception of the recall in the classification of dataset 'C,' FIG. 4 illustrates that all other average metrics in datasets 'A' and 'B' and direct metrics in datasets 'C' and MIMIC are above 0.9. The logistic regression classifier is, therefore, robust, since it yields high performance results, even on the classification of datasets from varying sources.

The classification of reports from varying sources described in this section refers only to the binary classification task. However, the same principle applies to multi-class classification and the analysis of reports from other sources (although the applicability could be limited by the availability of other data sources that present roughly the same 21 classes set forth above). It is also inferred that classification results might be affected if the distribution of classes varies significantly between the training and testing datasets, being that the latter is from an entirely different source.

Results presented above indicate that radiology reports can be efficiently classified by implementing ML-models. For example, with the exception of the logistic regression model implemented with TFIDF features, Tables report that that all F1 scores are above 0.82.

As noted above, the logistic regression classifier, implemented with word count features, outperforms the other evaluated classifiers. The logistic regression classifier yields the highest F1 score in the binary classification of the test set (Table III), in the classification of the unseen MIMIC dataset (Table V) and in the multiclass classification of the test set (Table IV and FIG. 3). The performance of the logistic regression classifier is followed by that of the SVM classifier (with word count features and a linear kernel), and lastly, by that of the decision tree classifier. Given the better performance of the linear classifiers (logistic regression, SVM), the data may be linearly separable, which could explain the slightly lower performance of the decision tree classifier.

The logistic regression binary classifier is also shown to generalize well to generating predictions for reports from different collections not seen during any development phase. This finding indicates that despite differences in writing styles and in report structures between radiologists and imaging institutions, CXR reports are characterized by a specific vocabulary that differs from the vocabulary commonly used to describe other types of exams, performed with other imaging modalities and on other anatomies.

TABLE VI

| Words with highest regression coefficients | Words with lowest regression coefficients |
| --- | --- |
| Chest, pleural, pulmonary, two lungs, cardiopulmonary, clear, silhouette, pneumothorax | Pain, contrast, seen, soft, was, cm, enlarged, there, ct |

Table VI, above, is directed to tokens detected in the binary classification CXR/non-CXR to which the classifier assigned the highest and lowest regression coefficients. The highest regression coefficients were assigned to words that strongly pushed the classification towards the positive class (CXR reports) while the presence of words with lowest coefficients biased the classification towards the negative class (non-CXR reports). The grouping of words illustrated in Table IV, above, recognizes that CXR reports are often referred to as chest two views, and they often describe conditions such as pleural effusion, pulmonary edema, clear lungs, or findings related to the cardiomediastinal silhouette or the presence/absence of pneumothorax. Inversely, reports of other imaging modalities, such as CT, may include descriptions of numerical measurements and their units (such as cm) and of the administration of contrast medications that increase the resolution and diagnostic capability of the images produced.

The empirical NLP-based model yields a relatively high F1 score of 0.88 in the binary classification of reports in the test set (Table III). This finding is somewhat expected since the training and testing datasets are part of the same report collection. However, when applied to the classification of reports in the MIMIC dataset, the NLP-based model fails to generalize to unseen collections (i.e., it yields a remarkably low recall). Though this model is not an efficient classifier overall, it can still yield precise predictions with very low rates of false positives. The extreme results (very high precision, very low recall) therefore suggest that this model was overfit to the training dataset.

The NLP-based model presented in this work is time consuming, subjective, dependent on human knowledge and experience, and probably not scalable to more than a few classes. It is developed, however, to provide an example of a classification algorithm that is not based on ML, and to provide a baseline for comparison with the performance of ML-based algorithms.

Accordingly, the ML models described herein facilitate the classification of radiology reports into two or more classes. In particular, embodiments described herein provide for the classification of radiology reports to identify modality and anatomy that is quickly approached with ML-based models that do not require complex feature engineering nor the fitting of classifier parameters or decision thresholds. These models yield high performance metrics and can also serve as classification baselines for the development of more complex models. In particular, among these ML-based models, the logistic regression classifier outperforms all other models in both classification tasks (binary and multiclass), achieving an average F1 score greater than 0.9. The logistic regression classifier is also robust, since it yields high performance metrics in the classification of reports from four sources different from the development dataset.

III. System Hardware and Implementation

Figure 5:
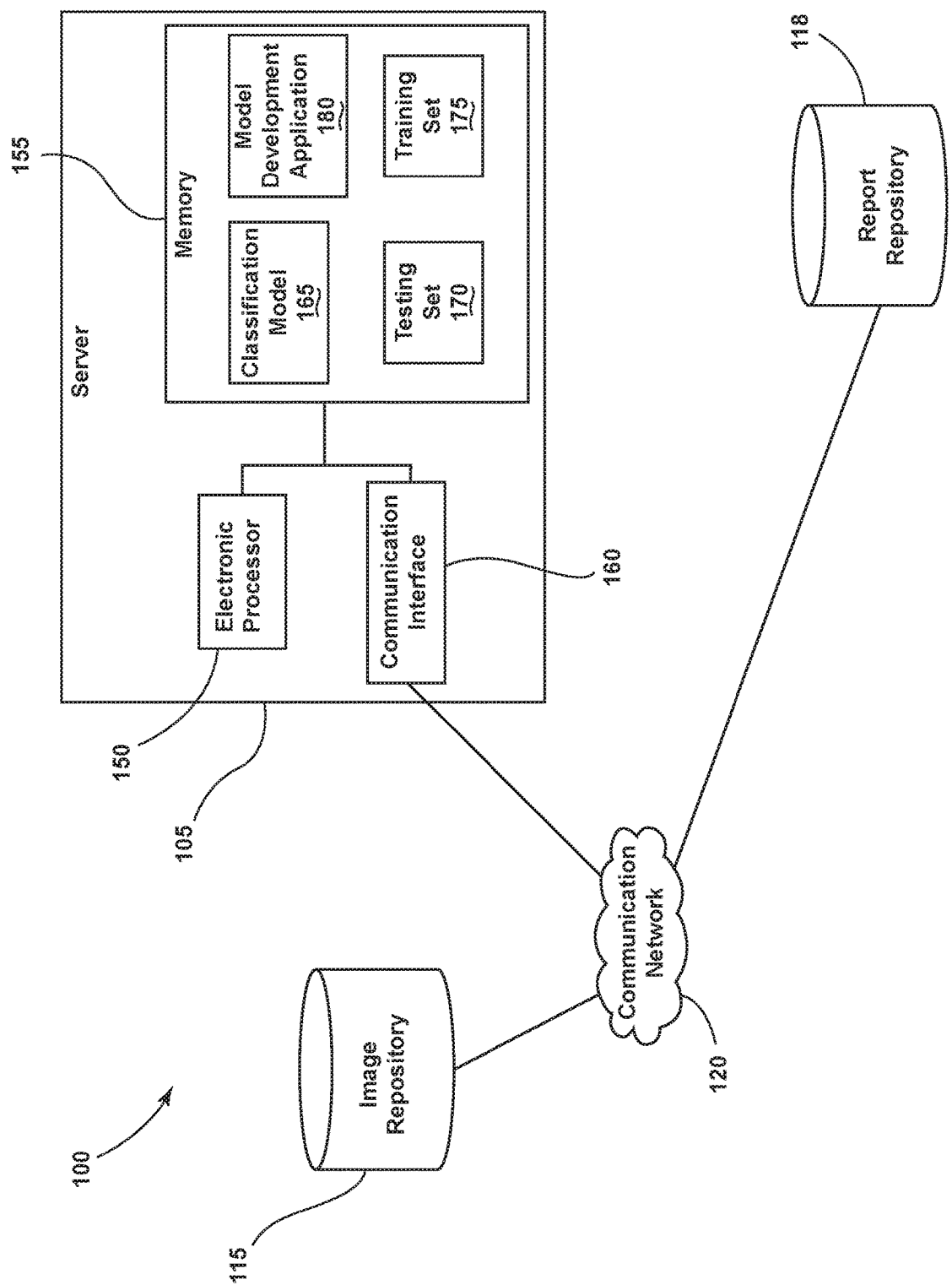
FIG. 5 illustrates a block diagram of a system for automatically classifying radiology reports according to one embodiment.

It should be understood that the functionality described herein above can be performed via one or more computing devices, such as one or more servers. For example, FIG. 5 illustrates a system 100 for developing (and executing) a classification model that includes a logistic regression classifier to predict anatomical focus and modality labels for reports as described herein according to some embodiments. As illustrated in FIG. 5, the system 100 includes a server 105, an image repository 115, and a report repository 118. The server 105, the image repository 115, and the report repository 118 communicate over one or more wired or wireless communication networks 120. Portions of the wireless communication networks 120 may be implemented using a wide area network, such as the Internet, a local area network, such as a Bluetooth™ network or Wi-Fi, and combinations or derivatives thereof. It should be understood that the system 100 may include more or fewer servers and the single server 105 illustrated in FIG. 5 is purely for illustrative purposes. For example, in some embodiments, the functionality described herein is performed via a plurality of servers in a distributed or cloud-computing environment. Also, in some embodiments, the server 105 may communicate with multiple image repositories or multiple reports repositories. Furthermore, in some embodiments, an image repository may be combined with a report repository and, in some embodiments, one or more of these repositories may be combined with the server 105. Also, in some embodiments, the components illustrated in the system 100 may communicate through one or more intermediary devices (not shown).

The image repository 115 stores images, including medical images. The image repository 115 may be, for example, a picture archiving and communication system (PACS), a cloud storage environment, or the like. The images stored in the image repository 115 are generated by an imaging modality (not shown), such as an X-ray computed tomography (CT) scanner, a magnetic resonance imaging (MRI) scanner, or the like. In some embodiments, the image repository 115 may also be included as part of an imaging modality.

The report repository 118 stores radiology reports for image studies, such as images stored in the image repository 115. For example, the report repository 118 may include a radiology information system (RIS), an electronic medical record (EMR) system, a hospital information system (HIS), or the like. Also, as noted above, in some embodiments, the report repository 118 includes a PACS and may be combined with the image repository 115. In some embodiments, only reports are processed, such that the system 100 may not need access to any images (via the image repository or otherwise). The report repository 118 provides access to a corpus of reports.

As illustrated in FIG. 5, the server 105 includes an electronic processor 150, a memory 155, and a communication interface 160. The electronic processor 150, the memory 155, and the communication interface 160 communicate wirelessly, over wired communication channels or buses, or a combination thereof. The server 105 may include additional components than those illustrated in FIG. 5 in various configurations. For example, in some embodiments, the server 105 includes multiple electronic processors, multiple memory modules, multiple communication interfaces, or a combination thereof. Also, it should be understood that the functionality described herein as being performed by the server 105 may be performed in a distributed nature by a plurality of computers located in various geographic locations. For example, the functionality described herein as being performed by the server 105 may be performed by a plurality of computers included in a cloud-computing environment.

The electronic processor 150 may be a microprocessor, an application-specific integrated circuit (ASIC), and the like. The electronic processor 150 is generally configured to execute software instructions to perform a set of functions, including the functions described herein. The memory 155 includes a non-transitory computer-readable medium and stores data, including instructions executable by the electronic processor 150. The communication interface 160 may be, for example, a wired or wireless transceiver or port, for communicating over the communication network 120 and, optionally, one or more additional communication networks or connections.

As illustrated in FIG. 5, the memory 155 of the server 105 includes a classification model 165, a testing set 170, and a training set 175, and a model development application 180. It should be understood that, in some embodiments, the functionality described herein as being provided by the classification model 165, the model development application 180, or both may be distributed and combined in various configurations, such as through multiple separate software applications. Similarly, although the testing set 170 and the training set 175 are illustrated in FIG. 5 as being included in the same memory 155, the testing set 170 and the training set 175 can be provided in different memories on the same or different devices in some embodiments.

As described above, the classification model 165 includes a ML-based classifier, such as, for example, a logistic regression, a decision tree classifier, or a SVM classifier, which is developed via the model development application 180 (via execution of instructions included in the application 180 by the electronic processor 150). The training set 175 includes a plurality of reports accessed via the report repository 118 and selected from the available corpus of reports. Similarly, the testing set 170 includes a plurality of reports accessed via the report repository 118 and selected from the available corpus of reports. In some embodiments, the testing set 170 includes a distinct set of reports than the training set 175.

As noted above, the model development application 180 uses the training set to develop the classification model 165. In particular, after selecting the training set 175 and the testing set 170 as described above, labels are assigned (e.g., manually) for an anatomical focus and a modality to the reports included in both sets 170 and 175. A sparse representation matrix is also extracted for each of the training set 175 and the testing set 170 based on, for example, features in the training set 175. The model development application 180 then learns a correlation between the features of the training set 175 and the corresponding labels (assigned to the reports included in the training set 175) using a machine learning classifier, thereby building the classification model 165.

In some embodiments, the model development application 180 also tests the classification model 165 on the reports in the testing set 170 for accuracy, such as by using the sparse representation matrix of the testing set 170. In particular, the model development application 180 can predict a label for one or more reports included in the testing set 170, which can be compared to the previously-assigned label. Differences between these labels can be used as feedback to adjust the classification model 165.

After developing and testing the classification model 165, the classification model 165 is used to predict anatomical focus and modality labels for other reports, such as the remaining reports in the corpus not included in the subset (i.e., not included in the training set 175 or the testing set 170). The accuracy of such predictions are described above. In some embodiments, the correctness of the predicted labels can be verified, such as by (i) performing unsupervised feature clustering on the remaining reports, thereby forming corpus clusters, (ii) measuring the compactness of the corpus clusters formed, (iii) performing unsupervised feature clustering on the reports in the training set, thereby forming training clusters, and (iv) measuring the overlap of the corpus clusters with the training clusters.

It should be understood that the systems and methods described herein are not limited to radiology reports but can be used with various types of reports associated with various types of images. Anatomical focus is an example of genre in the context of a radiology report.

Thus, embodiments described herein provide, among other things, methods and systems for automatically classifying radiology reports. In one embodiment, a logistic regression classifier may be applied by the systems and methods to quickly and effectively (e.g., with little or minimal user input or interaction) process radiology reports or the like that may include hundreds or thousands of images. Machine learning techniques may be used to establish or modify such classifying features, which further improve the efficiency and effectiveness of the systems and methods.

Various features and advantages of the embodiments are set forth in the following claims.

What is claimed is:

1. A method for developing a classification model, the method comprising:

selecting, from a corpus of reports, a subset of the reports from which to form a training set and a testing set;

assigning labels of a modality and an anatomical focus to the reports in both the training set and the testing set, wherein assigning labels of the modality and the anatomical focus to the reports including assigning a binary classification distinguishing chest x-ray reports from non-chest x-ray reports and, for each report labeled as a non-chest x-ray report, assigning a multi-class classification defining a modality associated with the report;

extracting a sparse representation matrix for each of the training set and the testing set based on features in the training set;

learning, with one or more electronic processors, a correlation between the features of the training set and the corresponding labels using a machine learning classifier, thereby building a classification model;

testing the classification model on the reports in the testing set for accuracy using the sparse representation matrix of the testing set; and predicting, with the classification model, labels of an anatomical focus and a modality for remaining reports in the corpus not included in the subset.

2. The method of claim 1, further comprising verifying the correctness of the predicted modality labels by:
(i) performing unsupervised feature clustering on the remaining reports, thereby forming corpus clusters;
(ii) measuring compactness of the corpus clusters formed;
(iii) performing unsupervised feature clustering on the reports in the training set, thereby forming training clusters; and
(iv) measuring overlap of the corpus clusters with the training clusters.

3. The method of claim 1, wherein extracting the sparse representation matrix for each of the training set and the testing set based on features in the training set includes extracting the sparse representation matrix for each of the training set and the test set based on term frequency-inverse document frequency (TFIDF) features in the training set.

4. The method of claim 1, wherein extracting the sparse representation matrix for each of the training set and the testing set based on features in the training set includes extracting the sparse representation matrix for each of the training set and the test set based on term frequency features in the training set.

5. The method of claim 1, wherein learning the correlation between the features and their corresponding labels using the machine learning classifier includes learning the correlation using a logistic regression classifier.

6. The method of claim 1, wherein learning the correlation between the features and their corresponding labels using the machine learning classifier includes learning the correlation using one selected from a group consisting of a logistic regression classifier, a decision tree classifier, and a support vector machine classifier.

7. The method of claim 1, wherein predicting, with the classification model, the labels of the anatomical focus and the modality for the remaining reports includes classifying each of the remaining reports as one selected from a group consisting of mammography, chest X-ray, obstetric ultrasound, spine magnetic resonance imaging (MRI), spine X-ray, bone densitometry analysis (DEXA), chest, abdomen and pelvis computed tomography (cap CT), abdomen ultrasound, leg venous Doppler ultrasound, feet and ankle X-ray, positron-emission tomography PET/CT tumor imaging, chest computed tomography (CT), breast ultrasound, knee Mill, hip X-ray, knee X-ray, brain MM, breast MM, and thyroid ultrasound.

8. The method of claim 1, wherein predicting, with the classification model, the labels of the anatomical focus and the modality for the remaining reports includes classifying each of the remaining reports as one selected from a group consisting of a chest X-ray report and a non-chest X-ray report.

9. A system for developing a classification model, the system comprising:
one or more electronic processors configured to:
select, from a corpus of reports, a subset of the reports from which to form a training set and a testing set,
assign labels of a modality and an anatomical focus to the reports in both the training set and the testing set, wherein assigning labels of the modality and the anatomical focus to the reports including assigning a binary classification distinguishing chest x-ray reports from non-chest x-ray reports and, for each report labeled as a non-chest x-ray report, assigning a multiclass classification defining a modality associated with the report,
extract a sparse representation matrix for each of the training set and the testing set based on features in the training set,
learn a correlation between the features of the training set and the corresponding labels using a machine learning classifier, thereby building a classification model,
test the classification model on the reports in the testing set for accuracy using the sparse representation matrix of the testing set, and
predict, with the classification model, labels of an anatomical focus and a modality for remaining reports in the corpus not included in the subset.

10. The system of claim 9, wherein the one or more electronic processors are further configured to verifying a correctness of the predicted modality labels by:
(i) performing unsupervised feature clustering on the remaining reports, thereby forming corpus clusters;
(ii) measuring compactness of the corpus clusters formed;
(iii) performing unsupervised feature clustering on the reports in the training set, thereby forming training clusters; and
(iv) measuring overlap of the corpus clusters with the training clusters.

11. The system of claim 9, wherein the features include frequency-inverse document frequency (TFIDF) features.

12. The system of claim 9, wherein the features include term frequency features.

13. The system of claim 9, wherein the machine learning classifier includes one selected from a group consisting of a logistic regression classifier, a decision tree classifier, and a support vector machine classifier.

14. The system of claim 9, wherein the predicted labels of the anatomical focus and the modality for the remaining reports includes one selected from a group consisting of mammography, chest X-ray, obstetric ultrasound, spine magnetic resonance imaging (MM), spine X-ray, bone densitometry analysis (DEXA), chest, abdomen and pelvis computed tomography (cap CT), abdomen ultrasound, leg venous Doppler ultrasound, feet and ankle X-ray, positron-emission tomography PET/CT tumor imaging, chest computed tomography (chest CT), breast ultrasound, knee Mill, hip X-ray, knee X-ray, brain Mill, breast MM, and thyroid ultrasound.

15. The system of claim 9, wherein the predicted labels of the anatomical focus and the modality for the remaining reports includes one selected from a group consisting of a chest X-ray report and a non-chest X-ray report.

16. A non-transitory, computer-readable medium storing instructions that, when executed by one or more electronic processors, perform a set of function, the set of functions comprising:
selecting, from a corpus of reports, a subset of the reports from which to form a training set and a testing set;
assigning labels of a modality and an anatomical focus to the reports in both the training set and the testing set, wherein assigning labels of the modality and the anatomical focus to the reports including assigning a binary classification distinguishing chest x-ray reports from non-chest x-ray reports and, for each report labeled as a non-chest x-ray report, assigning a multiclass classification defining a modality associated with the report;

extracting a sparse representation matrix for each of the training set and the testing set based on features in the training set;

learning a correlation between the features of the training set and the corresponding labels using a machine learning classifier, thereby building a classification model;

testing the classification model on the reports in the testing set for accuracy using the sparse representation matrix of the testing set; and predicting, with the classification model, labels of an anatomical focus and a modality for remaining reports in the corpus not included in the subset.

* * * * *